United States Patent [19]

Shehad et al.

[11] Patent Number: 5,023,376

[45] Date of Patent: Jun. 11, 1991

[54] REDUCTION OF NITROSAMINE FORMATION

[75] Inventors: Noel S. Shehad, Taylor Lake Village; Laurie L. Dussack, Friendswood, both of Tex.; Dirk van Hemelrijk, Antwerp, Belgium

[73] Assignee: Interox America, Houston, Tex.

[21] Appl. No.: 380,432

[22] Filed: Jul. 17, 1989

[51] Int. Cl.$^5$ .................. C07C 209/00; C07C 291/00; C07C 239/10; C07C 313/18

[52] U.S. Cl. .................................... 564/298; 540/474; 544/173; 546/184; 564/15; 564/76; 564/102; 564/300; 564/301

[58] Field of Search ............... 423/272, 273; 564/298, 564/300, 301, 102, 76, 15; 546/184; 544/173

[56] References Cited

U.S. PATENT DOCUMENTS

| | | | |
|---|---|---|---|
| 2,169,976 | 8/1939 | Guenther et al. | 260/561 |
| 2,419,283 | 4/1947 | Paul et al. | 260/306.6 |
| 2,795,611 | 1/1957 | List | 260/563 |
| 3,122,417 | 2/1964 | Blaser | 23/207.5 |
| 3,234,140 | 2/1966 | Irani | 252/186 |
| 4,144,272 | 3/1979 | Bergomi et al. | 260/567 |
| 4,247,480 | 1/1981 | Murata et al. | 564/298 |
| 4,304,762 | 12/1981 | Leigh | 423/272 |

FOREIGN PATENT DOCUMENTS

| | | |
|---|---|---|
| 307184A2 | 3/1989 | European Pat. Off. . |
| 7401261 | 8/1974 | Netherlands . |

*Primary Examiner*—Glennon H. Hollrah
*Assistant Examiner*—Peter G. O'Sullivan
*Attorney, Agent, or Firm*—Larson and Taylor

[57] ABSTRACT

Reaction of amine-containing substrates with hydrogen peroxide can suffer from the problems of in situ generation of nitrosamines, which are allegedly carcinogens, as impurities and impaired product formation, especially in the presence of transition metals.

The problems can be ameliorated by employing a selected range of alkyleneaminopoly(methylenephosphonic acid) compounds such as cyclohexane-1,2-diaminotetra(methylenephosphonic acid).

11 Claims, No Drawings

REDUCTION OF NITROSAMINE FORMATION

The present invention relates to a process for the reduction of nitrosamine formation during reaction of substrates containing an amine functionality and particularly reaction of secondary or tertiary amines.

BACKGROUND TO THE PRESENT INVENTION

One of the recognized methods of oxidizing secondary or tertiary amines comprises reacting the substrate with hydrogen peroxide, sometimes in the presence of a catalyst or other additives to promote the reaction. Thus, for example the addition of a chelating agent selected from EDTA or stannate together with carbonic acid or a carbonate has been suggested in U.S. Pat. Specification No. 4 247 480 to Nissan Chem Ind KK. Many other papers or patents also describe other variations to the reaction between amines and hydrogen peroxide.

However, there are two aspects of the hydrogen peroxide based processes to which insufficient attention has been paid hitherto, one aspect comprising the generation in situ of unwanted nitrosamine by-products and the second aspect comprising the impairment of production efficiency under non-ideal operating conditions.

In the first aspect, which in practice is often the more important aspect, the present investigations have shown that even when tertiary amines are being converted relatively efficiently to amine oxides, there is a distinct tendency for nitrosamines to be produced as a by-product. Their presence is disadvantageous for several reasons, including especially the fact that nitrosamines are carcinogenic as a class and less importantly the typical yellow color which they can impart to the normally white product, when present in relatively high concentrations, neither disadvantage being acceptable to discriminating customers for the product. Major uses of amine oxides include personal hygiene preparations, so that it is of practical significance to either prevent the formation of nitrosamines or subsequently remove them before the amine oxide is incorporated in such formulations.

We have observed that the reaction between amines and hydrogen peroxide can result in the product being noticeably colored yellow. Some, though probably not all of the yellowing can arise from the presence of nitrosamine compounds, and some from the presence of other colored impurities. Whilst the presence of a yellowing is often an indicator that nitrosamines are present, the absence of color is no guarantee that nitrosamines too are absent, because the human eye is not a sufficiently sensitive detector to distinguish between tolerable and excessive residual levels of nitrosamines; the material can appear reasonably white to the eye, but still contain excessive residual nitrosamines. It will of course be recognized that nitrosamines are normally formed in the oxidation process of tertiary amines via a secondary amine that is present as impurity in the feedstock or is generated in situ as a result of competing side reactions. Accordingly, the problem of nitrosamine production can constitute a similar or even greater problem when the substrate is essentially a secondary amine.

The second aspect can be of importance because our current investigations have also shown that the peroxide/amine reaction is sensitive to the presence of a number of interfering substances and especially transition metals. Such materials can be present as impurities in the reactants, possibly as a result of the method or their manufacture, or introduced in water added as diluent in the reaction mixture, or can be extracted from the pipework or walls of the reaction vessels or holding tanks or resulting from inadvertant ingress of foreign bodies such as dust. The net result of such substances being present is to reduce the yield of product, and substantial loss of reaction efficiency can be encountered in cases of gross contamination. Herein, when high levels of the interfering materials are present, the conditions are sometimes described as "stress conditions".

In practical operation of the reactions involving amines and hydrogen peroxide, the interfering substances are normally present as a result of causes other than their deliberate addition, which causes are often outside the direct control of the process user, so that he cannot simply predict whether or not the substances will be present. He could analyze every sample for impurities with a view to not employing those which failed to meet an empirically determined purity standard, but that would constitute an onerous and costly task. Accordingly, it would be of practical benefit to find a means that can ameliorate any detrimental effects of the interfering substances, a means which is employable all the time and which does not interfere with the reaction under more favorable operating conditions, sometimes referred to herein as "ideal" conditions.

Moreover, the two effects can occur together, so that what is really preferable would be a treatment or combination of compatible treatments which ameliorates or overcomes both problems.

OBJECTS OF THE INVENTION

It is an object of the present invention to reduce or suppress the formation of nitrosamines during reaction between hydrogen peroxide and substrate comprising a secondary or tertiary amine.

It is a second object of the present invention to enable the efficiency of production of an amine oxide from a tertiary amine to be improved under transition metal contaminated conditions without impairing efficiency of production under ideal conditions when the contamination from transition metals is less than significant or is completely absent.

These and other objects will be apparent from the general description of the invention and the specific embodiments provided hereinafter.

BRIEF DESCRIPTION OF THE INVENTION

According to the present invention there is provided an improved process for the reaction of a secondary or tertiary amine substrate with an aqueous solution of hydrogen peroxide, the improvement comprising carrying out the reaction in the presence of an effective amount of an alkylene aminomethylene phosphonic acid or water soluble salt thereof obeying either of the general formulae:

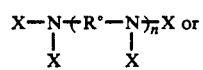   1.

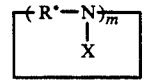   2.

in which

X represents a group of formula —$CH_2$—$PO_3My$ in which

M represents H or a non-transition metal cation conferring water-solubility,

Y represents 1 or 2,

R° represents an aliphati or alicyclic diradical of 2 or 3 carbon atoms length and containing from 2 to 6 carbon atoms, n represents an integer selected from 1 to 4 and m represents an integer selected from 4 to 6.

By the use of the afore-mentioned organic aminophosphonic acid compounds in an effective amount, it is possible to simultaneously ameliorate the problem of nitrosamine formation and improve the efficiency of amine oxidation in the presence of significant amounts of transition metals.

It will be recognized that the reaction involving the amine substrate may comprise simply its oxidation with hydrogen peroxide, or the reaction between hydrogen peroxide and some other functionality in the amine-containing substrate, such as the coupling of a diakylaminoalkanethionothiolic acid (also known as a dialkyldithiocarbamate) to form a thiuram, or may also involve reaction between the amine, hydrogen peroxide and a third reactant, as for example in the production of sulfenamides from a mercaptan, an amine and hydrogen peroxide.

MORE DETAILED DESCRIPTION OF SOME EMBODIMENTS

Within the range of organic phosphonic acid compounds encompassed within fcrmula 1 in the process of the instant invention, n is particularly suitably 1 or 2 and in compounds according to formula 2, m is preferably 4 or 6. For both formulae, adjacent amino groups are preferably separated by two linear carbon atoms which may bear simply hydrogen atoms or be substituted by a methyl group or form part of a 6 or 5 membered carbocyclic ring. It will be recognized that in such compounds, the length of the diradical is two carbon atoms. M can often represent a hydrogen atom or an alkali metal, ammonium or magnesium ion. Within formula 1, particularly preferred compounds include ethylenediaminetetra(methylenephosphonic acid), diethylenetriaminepenta(methylenephosphonic acid) and 1,2-cyclohexanediaminetetra(methylenephosphonic acid) and the corresponding fully or partly neutralized sodium, potassium or ammonium salts thereof. Other suitable aminophosphonic acid compounds are the cyclic compounds within formula 2 which include tetracyclenetetra(methylenephosphonic acid) and hexacyclenehexa(methylenephosphonic acid) and the corresponding fully or partly neutralized sodium, potassium or ammonium salts thereof.

The choice of such compounds is not arbitrary but is limited deliberately to the compounds that are able to attain the two objects of the invention to a reasonable extent. It is recognized and understood by the inventors that transition metals in particular may play a significant role in causing the problems which the instant invention seeks to ameliorate. It is acknowledged that chelation of transition metals in other circumstances has been practiced, for example to improve the long term storage stability of aqueous hydrogen peroxide solutions, but it was also evident to the inventors that the problems inherent in the production of amine oxides are more complex than can be cured inevitably by complexing the offending ions and are not simply identical to the problems inherent in stabilizing hydrogen peroxide solutions. This view is based upon the evidence that many chelating agents, even phosphonic acid-based chelating agents which are known to be able to chelate transition metal ions very well are significantly inferior in the context of ameliorating the problems described herein for amine oxide production. Thus, for example, the selection excludes (hydroxyethylidene)diphosphonic acid and hexamethylenediaminotetra(methylenephosphonic acid) and their salts, both of which are very good phosphonic acid based chelating agents for transition metals.

Expressed qualitatively, enough phosphonic acid compound needs to be present to enable it to attain the objectives of maintaining reaction efficiency and supressing nitrosamine formation from amines when deleterious substances such as transition metals are present in the reaction mixture. It will be recognized that there are various ways in which it is possible to express quantitatively the qualitative expression, enough. These alternative ways can achieve addition of phosphonic acid compound within broadly similar ranges, and can be used separately or together to achieve the most beneficial effect, at the discretion of the user. The way chosen as the basis for calculating the quantitative amount can take into account the likely principal source or sources of metal contamination and any likely fluctuations in reagent usage. For the avoidance of doubt, herein, unless otherwise indicated, concentrations and amounts are on the basis of the active phosphonic acid ingredient and ignore any diluent that may also be present in commercially available material.

Normally, the amount of phosphonic acid compound is at least $10^{-5}$ moles per mole of amine and often from $5 \times 10^{-3}$ to $10^{-3}$ moles per mole amine.

One simple basis comprises the total weight of the reaction mixture. The concentration of the phosphonic acid compounds is at least 15 ppm and desirably in the range of from 50 to 500 ppm, by which we mean parts by weight per million parts of the reaction mixture. It will be recognized that as concentrations rise from 15 to 50 ppm, the likelihood increases that the level of phosphonic acid compound will be able to retain reaction efficiency and suppress nitrosamine formation better for an increasingly large proportion of transition metal contaminations.

It will be recognized that the phosphonic acid compounds can be introduced into the reaction mixture as a separate component thereof, or and more conveniently, they can be incorporated together with one of the other components of the reaction mixture, such as for example the aqueous hydrogen peroxide feedstock solution. Naturally, the concentration of the phosphonic acid compounds in the hydrogen peroxide solution is selected in the light of the amount of hydrogen peroxide that it is intended to employ, and the concentration of hydrogen peroxide in the feedstock solution. Thus, to some extent, the concentration of the phosphonic acid compounds in the reaction mixture can vary depending upon the choice of amine being oxidized or its concentration in the reactant can be prior adjusted to make due allowance for reagent useage.

It is normally convenient to employ an aqueous hydrogen peroxide solution containing at least 0.03 parts by weight of phosphonic acid compound per 100 parts by weight of hydrogen peroxide discounting the weight of any diluent water, and in many instances, such as when producing the amine oxide from a tertiary amine which uses little more than equimolar hydrogen peroxide, it is convenient to employ a concentration of from 0.3 to 3 parts by weight of phosphonic acid compound per 100 parts by weight of hydrogen peroxide. Since the concentration of hydrogen peroxide feedstock employed is normally selected in the range of from 30 to 70% w/w, approximately, the phosphonic acid concentration therein is normally at least 100ppm and often from 350 to 7000 ppm by weight. If the hydrogen peroxide is also diluted before the reaction, then naturally its phosphonic acid content will be correspondingly diluted too. Such concentrations of phosphonic acid compounds constitute the provision of an effective amount in the reaction mixture for the purposes of the instant invention.

The instant invention is particularly appropriate for use in the oxidation of substrates containing a secondary or tertiary amine group. Particular reactions include the formation of amine oxides which obey

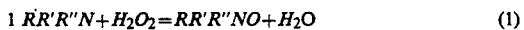

$$1 \quad RR'R''N + H_2O_2 = RR'R''NO + H_2O \quad (1)$$

but can also be used in reactions for making hydroxylamines

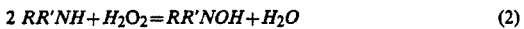

$$2 \quad RR'NH + H_2O_2 = RR'NOH + H_2O \quad (2)$$

The invention is also appropriate for reactions involving a third reactant, which reactions naturally permit the two component interaction between amine and hydrogen peroxide. One particular example thereof comprises the production of sulfenamides, the reaction being

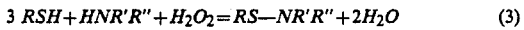

$$3 \quad RSH + HNR'R'' + H_2O_2 = RS-NR'R'' + 2H_2O \quad (3)$$

Where the amine containing substrate also contains a further functionality which reacts in the presence of hydrogen peroxide, this too can result in nitrosamine formation as an undesirable by-product. One example comprises

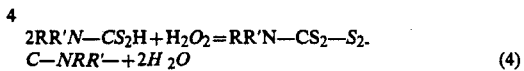

$$4$$
$$2RR'N-CS_2H + H_2O_2 = RR'N-CS_2-S_2-$$
$$C-NRR'-+2H_2O \quad (4)$$

The invention is applicable to any secondary or tertiary amine which can be oxidized using hydrogen peroxide. Thus, in particular it is applicable to amines in which the nitrogen substituents R, R' and R" each represent the same or different alkyl groups, each containing at least 1, often from 1 to 30 carbon atoms, and at least one of the groups can be a cycloalkyl group. The two groups R and R' can combine with each other and the nitrogen atom to form a heterocylic amine containing at least 4 carbon atoms, which optionally can itself be nuclearly substituted by an oxygen atom. One or more of the alkyl groups may have an aromatic substituent, e.g. dimethyl aniline. The aliphatic amine substrate can also contain an ethoxylate or propoxylate chain, containing from 1 to 15 units. The aliphatic or heterocyclic amine substrate normally contains from 2 up to 50 carbon atoms. In many instances, the molecular weight of the amine substrate will fall within the range of from 80 to 325, and many of which contain from 6 to 22 carbon atoms.

Suitable low molecular weight amine substrates include dimethylamine and n- or isobutyldimethylamine, and the corresponding diethylamine compounds. Others include di and tributylamine, and cyclopentyldimethylamine.

In a number of desirable starting materials, at least one of the substituents R, R' and R" in the amine comprises a substituent containing at least 6 carbon atoms such as from 8 to 18 carbons. Such a substituent can comprise a long chain alkyl or cycloalkyl group. The long chain alkyl substituent may be linear, branched, or further substituted by or otherwise include within its structure a cycloalkyl group. Particular mention is made of linear C8 to C16 alkyl groups. The cycloalkyl substituent may be substituted by a short or long chain alkyl group. The remaining substituent of R, R' and R", are often short length alkyl groups containing from 1 to 5 carbon atoms, and in many instances are conveniently methyl or ethyl substituents. Thus, in one subset of suitable amines R and optionally R' is a linear C8 to C16 alkyl group or cyclohexyl and R' and R", if present and not already described, are methyl or ethyl. Examples of such alkylamines include hexyldimethylamine, 2-ethylhexyldimethylamine, octyldimethylamine, decyldimethylamine, dodecyldimethylamine, tetradecyldimethylamine, hexadecyldimethylamine and octadecyldimethylamine. Other examples include decylbutylethylamine, hexadecylhexylmethylamine, trioctylamine, cyclohexyldimethylamine, dicyclohexylmethylamine and cyclododecyldimethylamine.

Suitable heterocyclic amines include piperidine and morpholine and alkyl N-substituted derivatives thereof, and especially those in which R" is methyl or ethyl.

The invention process preferably employs at least a stoichiometric amount of hydrogen peroxide. In practical applications, it is possible to employ a similar amount of peroxide to that which has hitherto been suggested in the art for reacting with the same substrate under "ideal" conditions. The benefit from incorporating the selected phosphonate compounds is accordingly obtained by reducing the nitrosamine contamination and enabling a high substrate conversion to be maintained even under non-ideal conditions, rather than by seeking to compensate for the reaction losses by increasing the mole ratio of peroxide to amine substrate. In consequence, for example, the mole ratio of peroxide to aliphatic or heterocyclic tertiary amines in reaction (1) is normally not greater than 4:1, often less than 2:1 and in many practical instances is selected in the range of from 1.05:1 to 1.2:1. For reactions (2), (3) and (4), the amount of hydrogen peroxide to the secondary amine is normally less than ten times the stoichiometric amount and is preferably from about twice to four times the stoichiometric amount, ie the mole ratio is preferably from 2:1 to about 4:1 in reaction (2) or (3), and from 1:1 to 2:1 for reaction (4).

The invention process is normally carried out at a temperature of above ambient and often at up to about 80° C. All or most of the reaction can conveniently be effected at a temperature within the range of 40° to 75° C. The reaction period is normally selected taking into account the reaction temperature and whether it is process (1), (2) or (3). In many instances, the period is chosen within the range of from 2 to 10 hours.

Having described the invention in general terms, specific embodiments will now be described in more detail by way of example only.

EXAMPLES 2, 3, 6 AND 7 AND COMPARISONS C1, C4 AND C5

These Examples and Comparisons were caried out using the following general method:

Dodecyldimethylamine (0.2012 moles, 42.94 g), sufficient water to bring the total reaction mixture to 150 g, ie approximately 92.85 g, and a small amount, 0.16 g, of a stock metal solution to provide a deleterious amount of transition metal impurities (ie stress conditions) were charged into a passivated 250 mL reaction flask, at ambient temperature.

The stock metal solution was obtained by dissolving $CuSO_4.5H_2O$, 0.393 g, $MnSO_4.H_2O$, 0.1475 g, $K_2CrO_4$, 0.0935 g, $Fe(NH_4)_2(SO_4)_2.6H_2O$, 3.5106 g, $AlK(SO_4)_2.12H_2O$, 8.791 g in 500 mL water (deionized) containing sulfuric acid solution, 20 mL of 10% w/w solution. It contained a total of 2350 ppm metals concentration. Thus, the concentration of metals in the reaction mixture was 2.5 ppm. A small amount of the selected phosphonate or other material was then introduced into the mixture to provide a mole ratio to the metal of about 4.3:1, except in Example 3 in which the phosphonate was pre-mixed with the hydrogen peroxide solution.

The reaction mixture was then heated to a temperature of 60° C. and stirred. During the subsequent 45 minutes, aqueous hydrogen peroxide solution, 50% w/w solution, stabilized by sodium pyrophosphate at 70 ppm calculated as $PO_4$, 15.03 g, was then delivered into the reaction mixture continuously. When all the hydrogen peroxide had been introduced, the reaction temperature was increased to 75° C. and the reaction permitted to continue for a total of 4 hours. The mixture was then cooled and analyzed, the results being summarized in Table 1 below. In Table 1, the abbreviations for the phosphonates employed were respectively:

DTPMP—diethylenetriaminepenta(methylenephosphonic acid), sodium salt, available from Monsanto under the Trade Mark "Dequest" grade 2066, ATMP—aminotris(methylenephosphonic acid) sodium salt, available from Monsanto under the Trade Mark "Dequest" grade 2006, CDTMP—cyclohexanediaminotetra(methylenephosphonic acid), sodium salt, a product developed by Interox Chemicals, and HCMP - hexacyclenehexa(methylenephosphonic acid) a development product of Interox.

The residual amounts of peroxide and amine are the measured amounts in the mixture, the A O yield indicated is the weight percentage of measured amine oxide based on the amount of amine employed, assuming a purity of 97.5% and the amine conversion is based on the weight of the amine material (as 100%) that has been consumed.

TABLE 1

| Ex/ Comp | Type of Phosphonate | Residual Peroxide wt % | Residual Amine wt % | A O yield wt % | Amine Conversion wt % |
|---|---|---|---|---|---|
| C 1 | none | 0.0 | 14.9 | 47.0 | 48.4 |
| Ex 2 | DTPMP | 0.72 | 1.6 | 96.2 | 94.4 |
| Ex 3 | " | 0.66 | 0.9 | 97.2 | 96.7 |
| C 4 | ATMP | 0.02 | 17.3 | 38.3 | 40.5 |
| C 5 | ATMP(7.3) | 0.02 | 9.9 | 63.1 | 65.7 |
| Ex 6 | CDTMP | 0.67 | 0.8 | 97.7 | 97.3 |
| Ex 7 | HCMP | 0.76 | 0.9 | 97.1 | 96.8 |

From Table 1, C1, it can be seen that under the stress conditions, the yield of amine oxide from the reaction could fall away in the absence of phosphonates. Moreover, it can also be seen that the presence of certain N-methylenephosphonate compounds resulted in very great amelioration of the problem, viz DTPMP, CDTMP and HCMP, whereas ATMP did not perform with similar effectiveness. Comparison C4, it will be noted, actually resulted in less amine conversion and a lower yield of amine oxide than the corresponding reaction to which no phosphonates had been introduced. This demonstrates very clearly that the role of the phosphonic acid compound is not merely that of stabilizing the hydrogen peroxide solution in order to improve the process, nor merely that of chelating metals such as iron and copper in solution, because ATMP is not only a very well known chelating agent for such metals, but is also a stabilizer for hydrogen peroxide solutions.

It can be seen that the three exemplified materials which improve the process in Ex2/3, Ex6 and Ex7 share a similarity with each other in that they each contain a plurality of amino nitrogen centres, each of which is substituted by at least one methylenephosphonate group. On the other hand, ATMP contains but a single nitrogen centre. Comparison C5 was conducted employing a much higher mole ratio of ATMP to metals than in the other trials, 7.3:1 instead of 4.3:1. It will be seen that this result was rather better than C4, but still very markedly worse than the results for Ex2/3, Ex6 or Ex7. This demonstrates that the difference in effectiveness for the present purpose is not explained simply on the basis of the number of methylenephosphonate groups in the molecule. A mole ratio of 7.3:1 for ATMP:metals provides an equivalent mole ratio 22:1 phosphonate groups:metal, whereas the mole ratio of 4.3:1 for DTPMP provides substantially the same equivalent mole ratio of 21.5:1. The difference between C5 and Ex2 clearly shows that this equivalent mole ratio is not the determining factor.

In Ex3, the same amount of DTPMP was used as in Ex2, but it had been pre-introduced into the hydrogen peroxide solution. It will be observed by comparing the results of EX2 and Ex3 that the material was equally as good, or possibly even slightly better when introduced via the hydrogen peroxide solution.

In addition to determining the effect of the phosphonates upon the extent of the reaction, the residual content of nitrosamines was independently measured by gas chromatography - thermal energy analyzer, and Table 2 below gives the sum of the two principal nitrosamines, namely dimethylnitrosamine and dodecylmethylnitrosamine.

TABLE 2

| Product obtained in | Residual Nitrosamines (ppb) |
|---|---|
| Ex 2 | 251 |
| Ex 6 | 1950 |
| Ex 7 | 1056 |
| C 1 | 4241 |
| C 4 | 11036 |

From Table 2, it can be seen that the invention phosphonates were able to lower the residual nitrosamine content substantially, whereas the non-selected ATMP was significantly worse.

EXAMPLES 8 TO 10 AND COMPARISONS C11 to C15

In these Examples and Comparisons, the general method of Example 2 to 7 was followed, except for the use of the specified chelating agents at the common mole ratio of 4.3:1 chelating agent:metals and in Example 10 the use of a lower mole ratio of 2.15:1. The abbreviations for the chelating agents used are as follows:

DTPMPA—the acid form of DTPMP

EDTMP—ethylenediaminetetra(methylene phosphonic acid), available from Monsanto under their Trade Mark "Dequest" grade 2041, HDTMP—hexamethylenediaminetetra(methylene phosphonic acid) available from Monsanto under their Trade Mark "Dequest" grade 2051, HEDP—hydroxyethylidene-1,1-diphosphonic acid, available from Monsanto under their Trade Mark "Dequest" grade 2010, EDTA—ethylenediaminetetra(acetic acid), sodium salt, DTPA—diethylenetriaminepenta(acetic acid), sodium salt, and CDTA—cyclohexane-1,2-diaminotetra(acetic acid), sodium salt.

The results are summarised in Table 3.

TABLE 3

| Ex/ Comp | Type of Phosphonate | Peroxide Consumed wt % | A O yield wt % | Amine Conversion wt % | Residual Nitrosamine ppb |
|---|---|---|---|---|---|
| Ex 8 | DTPMPA | 86.4 | 96.5 | 96.1 | 1591 |
| Ex 9 | EDTMP | 91.5 | 97.0 | 95.5 | 2477 |
| Ex 10 | DTPMP | 83.1 | 98.8 | 98.3 | 1031 |
| C 11 | HDTMP | 99.6 | 37.0 | 58.7 | 3834 |
| C 12 | HEDP | 99.6 | 32.1 | 48.2 | 10024 |
| C 13 | EDTA | 99.9 | 35.3 | 54.8 | 3421 |
| C 14 | DTPA | 99.6 | 83.9 | 83.2 | 7017 |
| C 15 | CDTA | 99.9 | 34.4 | 68.1 | 3279 |

From Table 3, the conclusions derived from Table 1 are confirmed. In addition, by comparing C11 with Ex8 or Ex9, it becomes apparent that the extent of separation of the amino groups in the phosphonate chelating agent is of considerable significance in determining its effectiveness for the present purpose. Separation of the amino groups by two methylene groups results in a very effective compound for the present purposes, as in Ex9, but if the number of methylene groups separating the amino groups is increased significantly to six, then the compound becomes singularly ineffective for present purposes. Similarly, the result of C12 shows that a commonly available hydroxy-substituted phosphonic acid compound is ineffective for the purposes of the present invention, even though it is a well established chelating agent and hydrogen peroxide stabilizer.

Comparisons C13 to C15 demonstrate that the aminoacetate compounds that correspond to the aminomethylenephosphonate compounds exemplified in Examples 2, 9 and 6 respectively are singularly less effective for the purposes of the instant invention than are the phosphonate compounds, in that the aminoacetate compounds all result in markedly impaired amine oxide yield, and worse consumption of hydrogen peroxide.

The results in Table 3 accordingly confirm that the selection of the chelating agent is of crucial importance in attaining the objects of the instant invention.

We claim:

1. In a process for the reaction of a secondary or tertiary amine-containing substrate with an aqueous solution of hydrogen peroxide, the improvement comprising carrying out the reaction in the presence of an effective amount of an alkyleneaminopoly(methylenephosphonic acid) or water soluble salt thereof obeying either of the general formulae:

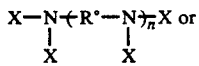

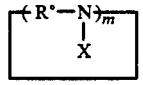

in which

X represents a group of formula —CH$_2$—PO$_3$M$_y$ in which

M represents H or a non-transition metal cation conferring water-solubility, Y represents 1 or 2, R° represents an aliphatic or alicyclic diradical of 2 or 3 carbon atoms length and containing from 2 to 6 carbon atoms, n represents an integer selected from 1 to 4 and m represents an integer selected from 4 to 6.

2. A process according to claim 1 in which the amount of alkyleneaminopoly(methylenephosphonic acid) or salt thereof is selected in the range of from 15 to 500 ppm w/w in the reaction mixture.

3. A process according to claim 1 in which the alkylene aminopoly(methylenephosphonic acid) or salt thereof is present in a mole ratio to the amine of from 1:20,000 to 1:1000.

4. A process according to claim 1 in which the alkyleneaminopoly(methylenephosphonic acid) or salt thereof is selected from formula 1 or 2 compounds in which R° represents a dimethylene diradical and respectively n is 1 or 2 or m is 4 or 6.

5. A process according to claim 1 in which the amine containing substrate is a secondary or tertiary amine of formula RR'R"N in which R and R' each represent an alkyl or cycloalkyl group and optionally at least one of which is substituted by an aromatic substituent or by an ethoxylate or propoxylate chain or in which R and R' combine with the N atom to form a heterocyclic nucleus and in which R" represents hydrogen, a functionality capable of reacting with hydrogen peroxide, an alkyl or cycloalkyl group.

6. A process according to claim 5 in which R in the amine containing substrate represents an alkyl group containing from 6 to 18 carbon atoms and R' and R" represent methyl or ethyl groups.

7. A process according to claim 5 in which the amine containing substrate is reacted with hydrogen peroxide in a mole ratio of the latter to the former of from 1.05:1 to 1.2:1.

8. A process according to claim 1 in which the amine-containing substance comprises a secondary or tertiary amine.

9. A process according to claim 1 in which the amine-containing substance comprises a tertiary amine.

10. A process according to claim 1, wherein said aqueous hydrogen peroxide solution contains at least 0.03 parts by weight of said alkyleneaminopoly(methylenephosphonic acid) per 100 parts by weight of hydrogen peroxide.

11. A process according to claim 10 in which the alkylene aminopoly(methylenephosphonic acid) or salt thereof is present in a weight ratio of from 0.3 to 3 parts w/w per 100 parts of hydrogen peroxide that is introduced into the reaction mixture.

* * * * *